United States Patent [19]
Mackin

[11] Patent Number: 5,285,778
[45] Date of Patent: Feb. 15, 1994

[54] ENDOTRACHEAL TUBE WIH FIBERS OPTIC ILLUMINATION AND VIEWING AND AUXILIARY TUBE

[76] Inventor: Robert A. Mackin, 1033 Lake Point, Flagstaff, Ariz. 86004

[21] Appl. No.: 912,031

[22] Filed: Jul. 9, 1992

Related U.S. Application Data

[63] Continuation of Ser. No. 688,643, Apr. 19, 1991, abandoned.

[51] Int. Cl.$^5$ .............................................. A61M 16/00
[52] U.S. Cl. ............................ 28/207.15; 128/207.14; 128/200.26
[58] Field of Search ........................................ 128/4–6, 128/11, 200.26, 207.14, 207.15

[56] References Cited

U.S. PATENT DOCUMENTS

| | | | |
|---|---|---|---|
| 3,322,126 | 5/1967 | Rusch et al. | 128/351 |
| 3,498,286 | 3/1970 | Polanyi et al. | 128/2 |
| 3,669,098 | 6/1972 | Takahashi | 128/6 |
| 3,677,262 | 7/1972 | Zukowski | 128/6 |
| 3,776,222 | 12/1973 | Smiddy | 128/6 |
| 3,866,599 | 2/1975 | Johnson | 128/2 |
| 3,913,568 | 10/1975 | Carpenter | 128/11 |
| 4,041,936 | 8/1977 | Carden | 128/6 |
| 4,086,919 | 5/1978 | Bullard | 128/6 |
| 4,327,720 | 5/1982 | Bronson et al. | 128/207.15 |
| 4,567,882 | 2/1986 | Heller | 128/11 |
| 4,742,819 | 5/1988 | George | 128/6 |
| 4,819,664 | 4/1989 | Nazari | 128/207.15 |
| 4,846,153 | 7/1989 | Berci | 128/6 |
| 4,850,371 | 7/1989 | Broadhurst et al. | 128/207.14 |
| 4,896,941 | 1/1990 | Hayashi et al. | 128/6 |
| 4,949,716 | 8/1990 | Chenoweth | 128/207.14 |
| 4,958,932 | 9/1990 | Kegelman et al. | 128/6 |

Primary Examiner—Edgar S. Burr
Assistant Examiner—Aaron J. Lewis
Attorney, Agent, or Firm—Cahill, Sutton & Thomas

[57] ABSTRACT

An endotracheal tube includes a main tube having a proximal end portion and a distal end portion, an inflatable annular cuff disposed on the main tube in sealed relation thereto adjacent on the distal end portion. An inflation tube extends from the distal end portion into the cuff. A viewing lens is located on the distal end portion and optically coupled to a first optical fiber extending from the proximal end portion to the distal end portion. A viewing device is attached to a proximal end of the first optical fiber. An illumination port is located on the distal end portion coupled to a second optical fiber extending from the proximal end portion to the distal end portion. An illumination source is optically coupled to a proximal end of the second optical fiber. The extended insertion of the endotracheal tube and conditions of adjacent tissue can be viewed by means of the viewing device. A flushing tube extends from a flushing source adjacent to the proximal end portion to a flushing outlet port located at the distal end portion adjacent to the viewing lens to flush mucous away from the viewing lens. In one embodiment, an auxiliary tube extends through a sealable port in a wall of the proximal end portion and slides through the sealable port, through the main tube and out of the distal end portion thereof. The auxiliary tube includes fiber optic illumination and viewing elements on a distal end portion thereof and an inflatable annular cuff on the distal end portion thereof.

7 Claims, 1 Drawing Sheet

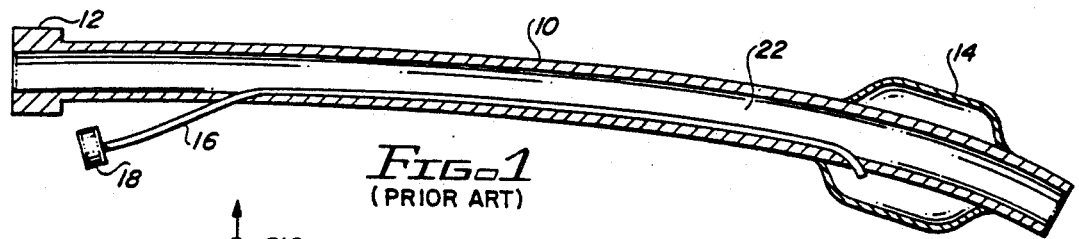
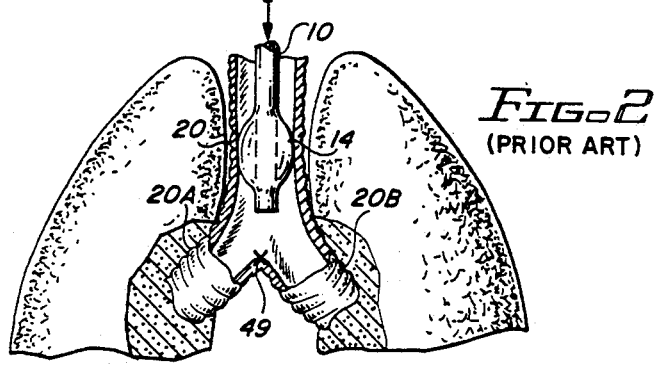
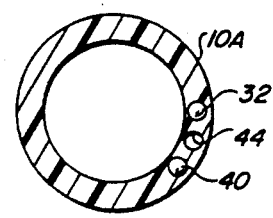
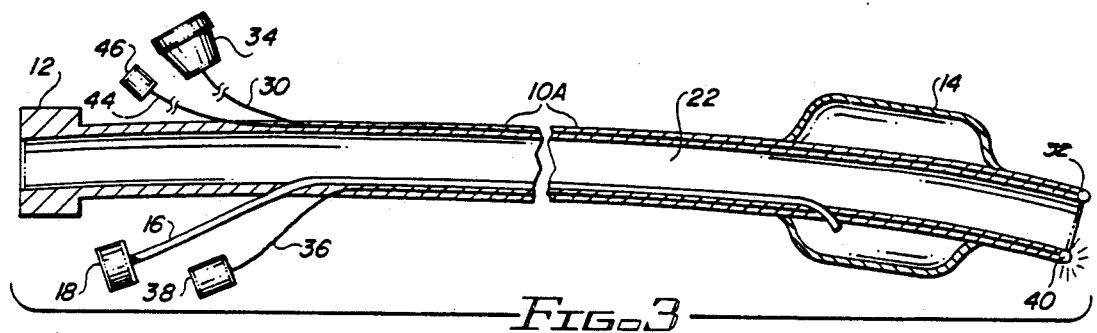
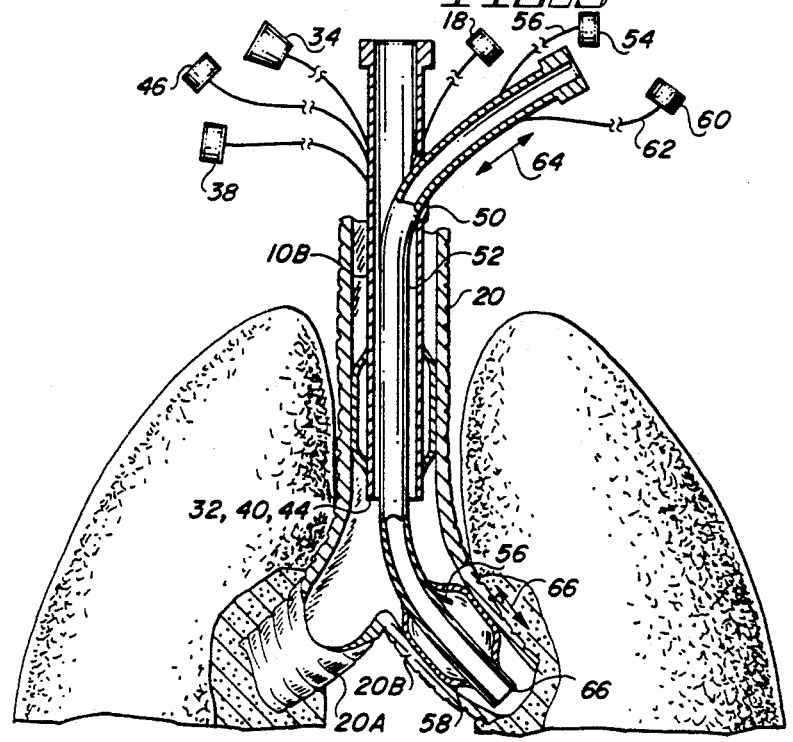

ENDOTRACHEAL TUBE WIH FIBERS OPTIC ILLUMINATION AND VIEWING AND AUXILIARY TUBE

This application is a continuation of my co-pending application Ser. No. 688,643, filed on Apr. 19, 1991, now abandoned, entitled "Endotracheal tube with fiber optic illumination and viewing and auxiliary tube".

BACKGROUND OF THE INVENTION

The invention relates to endotracheal tubes, and more particularly to fiber optic illumination and viewing of the distal end of the endotracheal tube. The invention also relates to an auxiliary tube slidably disposed in the endotracheal tube for occluding one main stem bronchus while permitting ventilation of a lung through the other.

FIG. 1 shows a conventional endotracheal tube 10. It includes a connector 12 by means of which endotracheal tube 10 is connected to a conventional ventilator to assist a patient's breathing function. Endotracheal tube 10 also includes an inflatable balloon 14 on its distal end. Inflatable balloon 14 is inflated by means of a tube 16 which is connected by means of a end connector 18 to a small syringe-like air pump after the endotracheal tube 10 has been inserted into the patient's trachea 20, as shown in FIG. 2. In FIG. 2, balloon 14 is shown inflated, so that it occludes passage of air between the outer surface of endotracheal tube 10 and the inner surface of trachea 20. The ventilator can then efficiently pump air into and out of the patient's lungs.

Prior endotracheal tubes do not permit any visualization of what is going on in the patient's tracheal and bronchial passages. If such visualization is needed, the connector 12 (FIG. 1) is disconnected from the ventilator, and a conventional bronchoscope is inserted down the hollow passage 22 of endotracheal tube 2, allowing the physician to determine if a lot of mucous is present in either lung or in either of the left or right main stem bronchi 20A and 20B. If it is necessary to suction mucous out of either of the patient's lungs, a suctioning tube is inserted down the hollow passage 22 of endotracheal tube 10. The endotracheal tube may have to be disconnected from the ventilator to allow visualization in the trachea 20 of the lungs or to allow suctioning of mucous, blood, etc., if the endotracheal tube does not have a sealable side port through which the suctioning tube can be inserted.

A skilled physician, often a pulmonologist, inserts an endotracheal tube into a patient. It would be desirable for a nurse to be able to easily monitor the position of an endotracheal tube in a patient's trachea to determine if its location has been shifted so the nurse knows whether to call a physician for repositioning of it. It is also desirable to be able to determine accurately the position of an endotracheal tube without requiring an x-ray.

It should also be noted that prior bronchoscopes are complex, expensive instruments, typically costing $3,000 to $6,000.

SUMMARY OF THE INVENTION

It is an object of the invention to allow visualization of the tracheal tube and main stem bronchi and/or lungs of a patient without inserting a bronchoscope through an endotracheal tube.

It is another object of the invention to allow accurate insertion of an endotracheal tube without the need for taking x-rays of the patient.

It is another object of the invention to provide an inexpensive endotracheal tube having the capability of illumination and visualization at its distal end.

It is another object of the invention to provide an endotracheal tube which allows suctioning of one lung without interrupting ventilation of the other.

Briefly described, and in accordance with one embodiment thereof, the invention provides an endotracheal tube including a main tube having a proximal end portion and a distal end portion, an inflatable annular cuff disposed on the main tube in sealed relation thereto adjacent on the distal end portion, an inflation tube extending from the distal end portion into the cuff, a viewing lens located on the distal end portion and optically coupled to a first optical fiber extending from the proximal end portion to the distal end portion, a viewing device attached to a proximal end of the first optical fiber, an illumination port located on the distal end portion coupled to a second optical fiber extending from the proximal end portion to the distal end portion, and an illumination source optically coupled to a proximal end of the second optical fiber. The extended insertion of the endotracheal tube and conditions of adjacent tissue can be viewed by means of the viewing device. A flushing tube extends from a flushing source adjacent to the proximal end portion to a flushing outlet port located at the distal end portion adjacent to the viewing lens to flush mucous away from the viewing lens. In one embodiment, an auxiliary tube extends through a sealable port in a wall of the proximal end portion and slides through the sealable port, through the main tube and out of the distal end portion thereof. The auxiliary tube includes fiber optic illumination and viewing elements on a distal end portion thereof and an inflatable annular cuff on the distal end portion thereof.

BRIEF DESCRIPTION OF THE DRAWINGS

FIG. 1 is a section view diagram of a conventional endotracheal tube.

FIG. 2 is a partial section view diagram illustrating use of the endotracheal tube of FIG. 1.

FIG. 3 is a partial section view of an endotracheal tube of the present invention.

FIG. 3A is a distal end view of the endotracheal tube of FIG. 3.

FIG. 4 is a partial section view illustrating another endotracheal tube of the present invention and its use.

DETAILED DESCRIPTION OF THE PREFERRED EMBODIMENT

Referring next to FIG. 3, one embodiment of the present invention is shown, in which an improved endotracheal tube 10A has been modified to include an optical fiber 30 that extends through endotracheal tube 14 to a viewing lens 32 at its distal end. The optical fiber 30 can be an inexpensive plastic optical fiber, which costs only a few dollars, embedded in the wall of endotracheal tube 10A. A suitable viewing means, such as an eyepiece 34, is connected to the proximal end of optical fiber 30.

A second plastic optical fiber 36 that is connected at its proximal end to a high intensity light source 38 extends through the wall of endotracheal tube 10A to an illumination port 40 on the distal end of endotracheal tube 10A. As shown in FIG. 3A, viewing lens 32 and illumination port 40 can be located close together.

FIG. 3A is a distal end view of endotracheal tube 10A. A hollow tube 44 extends from a flushing inlet port connector 46 and extends through endotracheal tube 10A so that transparent saline flushing liquid can be forced through tube 44 to wash mucous away from viewing lens 32 and illumination port 40. Such mucous may collect thereon during insertion into the patient's trachea or afterward.

One major advantage of the endotracheal tube 10A is that the carina (a cartilaginous structure) designated by 49 in FIG. 2 can be easily viewed through viewing means 34 during insertion of endotracheal tube 10A, so that the nurse or physician can easily determine how far into the patient's trachea to properly insert endotracheal tube 10A. This avoids the need for an x-ray process to determine if this endotracheal tube is properly inserted. The endotracheal tube can become malpositioned in the patient, requiring a later x-ray to check proper placement of the endotracheal tube. The direct visualization afforded by the present invention can avoid the need for such a repeat x-ray. Another advantage is that the physician or nurse can easily view the conditions in branches 20A and 20B of the trachea 20 to determine the presence of mucous or other condition and determine whether there is a need for immediate suctioning of mucous, blood, etc. from either lung or the passages thereto.

In accordance with another embodiment of the invention, shown in FIG. 4, endotracheal tube 10B has all of the features of endotracheal tube 10A of FIG. 3, and further includes a sealing insertion port 50 through which a suctioning tube 52 can be inserted. A seal is maintained between the inserted suctioning tube 52 and insertion port 50. Suctioning tube 52 includes a hollow tube 56 connected to an inflation port 54, and extends to an inflatable balloon 58 on the distal end of suction tube 52.

Thus, suctioning tube 52 can be inserted through sealable insertion port 50 and can be inserted into one of the branches 20A or 20B of the patient's trachea 20, as shown in FIG. 4. The balloon 58 then can be inflated via inflation connector 54 and inflation tube 56, as shown in FIG. 4, to occlude the space between the outer surface of suction tube 52 and the inner surface of branch 20B of the bronchus.

Suction tube 52 also can have additional features 60 and optical fibers and flushing tubes collectively designated by numeral 62 to allow visualizing through appropriate lenses and port 66 to determine the conditions in branch 20B of the trachea 20 and in the lung connected thereto.

Furthermore, the ventilator can be left connected to endotracheal tube 10B, and the left lung can continue to be ventilated by the ventilator while the right lung is being occluded. This is a function that has never previously been achievable.

I constructed a prototype endotracheal tube similar to the one of FIG. 3. I then passed the prototype endotracheal tube into the trachea of an anesthetized live adult dog. The illumination and direct visualization afforded by the prototype allowed easy visualization and correct placement of the prototype endotracheal tube and allowed easy visualization to direct proper placement of a suction tube through the core of the endotracheal tube and into either the right or left main stem bronchus of the dog. The tracheal "rings" of the interior of the trachea were easily observable during introduction of the prototype, making it easy to avoid accidental insertion into the esophagus. The carina, a cartilaginous structure, was easily observable to allow correct depth of insertion.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention.

What is claimed is:

1. An endotracheal tube including means for lungs beyond the endotracheal tube during and/or after intubation continuous illumination and continuous viewing of the position of the endotracheal tube in the patient's trachea and conditions of portions of the trachea and lungs beyond the distal end portion of the endotracheal tube without either disconnecting a ventilator from the endotracheal tube or inserting a bronchoscope or endoscope through the endotracheal tube, the endotracheal tube comprising in combination:
   (a) a main tube having a proximal end portion and a distal end portion, an inflatable annular cuff being disposed on the main tube in sealed relation thereto adjacent to the distal end portion;
   (b) an inflation tube extending from the proximal end portion into the cuff;
   (c) integral means for avoiding problems in monitoring of the position of the endotracheal tube in a patient's trachea and conditions of portions of the trachea and lungs beyond the distal end portion during and/or after intubation of the endotracheal tube caused by use of an endoscope or bronchoscope extending through the endotracheal tube, the integral means including
      i. a viewing lens located on and directly attached to the distal end portion and optically coupled to a first optical fiber integral with the main tube and extending from the proximal end portion to the distal end portion,
      ii. a viewing device attached to a proximal end of the first optical fiber, and
      iii. an illumination port located in the distal end portion coupled to a second optical fiber integral with the main tube and extending from the proximal end portion to the distal end portion, a proximal end of the second optical fiber being optically coupled to an illumination source.

2. The endotracheal tube of claim 1 including a flushing tube extending from a flushing source adjacent to the proximal end portion to a flushing outlet port located at the distal end portion adjacent to the viewing lens to flush mucous away from the viewing lens.

3. The endotracheal tube of claim 2 including a sealable port in a wall of the proximal end portion and an auxiliary tube extending slidably through the sealable port, through the main tube and out of the distal end portion thereof, the auxiliary tube including fiber optic illumination and viewing means on a distal end portion thereof and an inflatable annular cuff on the distal end portion thereof.

4. A method of avoiding problems caused by use of an endoscope or bronchoscope in an endotracheal tube by using the endotracheal tube to visualize a patient's trachea and conditions in the patient's lungs without using an endoscope or bronchoscope, the method comprising the steps of:
- (a) inserting a distal end portion of the endotracheal tube into a patient's throat, the endotracheal tube having a proximal end portion and an inflatable annular cuff disposed on the endotracheal tube in sealed relation thereto adjacent to the distal end portion;
- (b) illuminating the interior of the trachea as the distal end portion is inserted by means of an illumination port located on the distal end portion and coupled to a distal end of a first optical fiber integral with the endotracheal tube and extending from the proximal end portion to the distal end portion and an illumination source optically coupled to a proximal end of the first optical fiber;
- (c) viewing the interior of the trachea as the distal end portion is inserted and viewing illuminated portions of the trachea and lungs beyond the distal end portion after the inserting by means of a viewing lens located on the distal end portion and optically coupled to a distal end of a second optical fiber integral with the endotracheal tube and extending from the proximal end portion to the distal end portion and a viewing device attached to a proximal end of the second optical fiber;
- (d) inflating the cuff by pumping gas into an inflation tube extending from the proximal end portion into the cuff after the viewing of step (c) verifies that the distal end portion is properly located relative to the patient's carina; and
- (e) continuing to monitor the position of the endotracheal tube in a patient's trachea and portions of the trachea and lungs beyond the distal end portion after intubation of the endotracheal tube by illuminating the portions of the trachea and lungs beyond the distal end portion by means of the illumination port, the first optical fiber, and the illumination source and by viewing the portions of the trachea and lungs beyond the distal end portion by means of the viewing lens, second optical fiber, and the viewing device, wherein continuing illumination and viewing of the endotracheal tube in the patient's trachea and conditions of portions of the trachea and lungs beyond the distal end portion area accomplished without disconnecting a ventilator from the endotracheal tube or inserting a bronchoscope or endoscope through the endotracheal tube.

5. The method of claim 4 including flushing mucous away from the viewing lens by means of a flushing tube extending from a flushing source adjacent to the proximal end portion to a flushing outlet port located at the distal end portion adjacent to the viewing lens.

6. The method of claim 5 including inserting an auxiliary tube slidably through a sealable port in a wall of the proximal end portion, through the main tube and out of the distal end portion thereof, the auxiliary tube including fiber optic illumination and viewing means on a distal end portion thereof and an inflatable annular cuff on the distal end portion thereof, and viewing the inside of a first main stem bronchus as the distal end portion of the auxiliary tube advances into the first main stem bronchus by means of the fiber optic illumination and viewing means until the cuff on the distal end portion of the auxiliary tube is properly located in the first main stem bronchus, and inflating the cuff on the distal end portion of the auxiliary tube to occlude the first main stem bronchus.

7. The method of claim 6 including ventilating a lung of the patient through a second main stem bronchus while the first main stem bronchus is occluded.

* * * * *